US007252981B1

(12) United States Patent
Ramakrishna et al.

(10) Patent No.: US 7,252,981 B1
(45) Date of Patent: Aug. 7, 2007

(54) METHOD FOR THE PREPARATION OF STABLE AND REUSABLE BIOSENSING GRANULES

(75) Inventors: Sonti Venkata Ramakrishna, Andhra Pradesh (IN); Srenivasulureddy Venkata Mohan, Andhra Pradesh (IN); Reddy Shetty Prakasham, Andhra Pradesh (IN); Palle Komaraiah, Andhra Pradesh (IN); Kondapuram Vijaya Raghavan, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 0 days.

(21) Appl. No.: 09/652,753

(22) Filed: Aug. 31, 2000

(51) Int. Cl.
  *C12P 7/14* (2006.01)
  *C12N 11/02* (2006.01)
  *C12N 1/02* (2006.01)

(52) U.S. Cl. ............... 435/162; 435/162; 435/177; 435/261

(58) Field of Classification Search ............ 435/4, 435/7.1, 7.32, 29, 30, 40.5, 40.51, 41, 170, 435/174, 176–178, 180, 182, 261, 262, 262.5, 435/800, 814, 818, 821, 962, 39; 210/613, 210/616, 620, 623, 626, 628; 436/62, 138, 436/175, 176, 518, 523, 524, 528, 529, 533, 436/534
See application file for complete search history.

(56) References Cited

U.S. PATENT DOCUMENTS

| 4,355,111 | A | * | 10/1982 | Shimizu et al. | 435/243 |
|---|---|---|---|---|---|
| 4,778,630 | A | * | 10/1988 | Moreton et al. | 554/221 |
| 4,996,150 | A | * | 2/1991 | Joung et al. | 435/161 |
| 5,405,764 | A | * | 4/1995 | Harder et al. | 435/161 |
| 5,697,186 | A | * | 12/1997 | Neyra et al. | 424/93.3 |
| 5,952,188 | A |   | 9/1999 | Kumar et al. | 435/14 |
| 5,990,191 | A | * | 11/1999 | Kikuta et al. | 522/87 |
| 6,153,416 | A | * | 11/2000 | Yuan | 210/601 |
| 6,337,019 | B1 | * | 1/2002 | Razavi-Shirazi | 210/610 |
| 6,361,695 | B1 | * | 3/2002 | Husain et al. | 210/195.2 |
| 6,420,146 | B1 | * | 7/2002 | Ramakrishna et al. | 426/62 |
| 6,461,511 | B1 | * | 10/2002 | Baba et al. | 210/616 |
| 6,471,864 | B1 | * | 10/2002 | Sublette et al. | 210/616 |

FOREIGN PATENT DOCUMENTS

| GB | 1586291 | 3/1981 |
|---|---|---|
| JP | 05192132 | 8/1993 |

OTHER PUBLICATIONS

Ramakrishna et al. Microbial fermentations with immobilized cells; whole cell immobilization and application in antibiotic, alcohol, enzyme, etc. production; a review. Curr. Sci. (1999) vol. 77, No. 1, pp. 87-100.*
Chemical Abstracts No. 116: 200304c vol. 116, No. 20, (1992) "Dry Preservation of Immobilized Activated Sludge" XP-002166471.
Riedel, K., et al. "A fast estimation of biochemical oxygen demand using microbial sensors" Applied Microbiology and Biotechnology, vol. 28, p. 316-318, (1988).
Derwent Abstract No. 1992-312516, XP-002166472 & JP 04218373, Aug. 7, 1992.
Heitkamp, M.A., et al. "Evaluation of five biocarriers as supports for immobilized bacteria: comparative performance . . . shocking" Environmental Toxicology and Chemistry, vol. 12, p. 1013-1023, (1993).

\* cited by examiner

*Primary Examiner*—Long V. Le
*Assistant Examiner*—Unsu Jung
(74) *Attorney, Agent, or Firm*—Ladas and Parry LLP

(57) ABSTRACT

The present invention provides a process for the preparation of stable and reusable biosensing granules useful in the assessment of biodegradability of effluents. The biosensing granules are prepared by culturing active aerobic microbial consortia in synthetic medium, separating the active aerobic microbial consortia, immobilizing the microbial consortia using natural polymer to form biosensing granules, and dehydrating the immobilized biosensing granules to obtain stable biosensing granules having a moisture content of 5-30%.

16 Claims, No Drawings

METHOD FOR THE PREPARATION OF STABLE AND REUSABLE BIOSENSING GRANULES

FIELD OF THE INVENTION

The present invention relates to a method for the preparation of stable and reusable biosensing granules useful for assessing the biotreatability of effluents.

BACKGROUND OF THE INVENTION

The present invention of development of biosensing granules will help in rapid characterisation of any effluent at on-site. Moreover, the invented biosensing granules are reusable for several times and involve less manpower. In addition, these biosensing granules are ecofriendly in nature, cost-effective and do not require any chemical or energy input and are hence easy to operate at field conditions.

The byproduct liquid streams from various industries contain different environmentally undesirable chemical compounds that adversely affect water bodies and groundwater reservoirs. The reduction of organic pollutants to environmentally acceptable limits is essential before discharging these effluents into the environment. This requires a prerequisite of measurement of organic content in these discharges, which help is estimation of pollutant strength, design of treatment methodology and disposable alternative, etc. The biodegradable organic strength in an effluent can be determined by calculating the ratio of biological oxygen demand (BOD) to chemical oxygen demand (COD). The prolonged time of analysis, undependable simulated experimental conditions and toxic nature of effluents limits its utilisation and subsequent decision making for selection of appropriate treatment methodology at on-site.

Effluent treatment options can be generally divided into the following categories—physical, chemical, biological and thermal. Among the above categories, biological treatment processes possess an edge over the others due to its potential to degrade the organic pollutants into simple and environmentally safe compounds such as methane, carbon dioxide and water that are eco-friendly in nature. Biotreatment of an effluent can be done by inoculation of appropriate microbial consortia and incubating either in anaerobic or aerobic conditions. Under aerobic conditions, microbial consorts present in the system utilise the oxygen and organic compounds of effluent for energy generation. The pollution concentration can be assessed by calculating the microbial activity in waste water. Thus, microbial activity in terms of respiration is an important indication to characterise the effluents under different biotreatability classes.

Several attempts have been made in part to determine the organic content of industrial effluents by chemical as well as by biological means so as to characterise the effluent, evaluate its biodegradability, and for choosing the appropriate treatment process option [Rogers, K. R. and Williams, L. R. (1995) Trends Anal. Chem. 14; 289-294]. The organic content of an effluent is generally expressed in terms of the amount of oxygen required to degrade the organic pollutants and is measured either by chemical or biological means. One of the thumb rules used in assessing the effluent's biotreatability criteria is the ratio of the biological oxygen demand (BOD) to that of the chemical oxygen demand (COD), which is normally a fraction. A low value of the BOD/COD ratio indicates the difficulty in biodegradation, while a high value represents the amicability of the wastes for biological degradation.

Biochemical oxygen demand is basically a bioassay procedure involving the estimation of oxygen consumed in a simulated system under standard prescribed conditions. BOD is performed in a BOD bottle of 300 ml capacity at 20° C. for 5 days by taking suitable aliquots of effluents in the presence of seed, either from raw sewage or treated effluent from waste water treatment plant and nutrients. The long time taken for analysis, undependable simulated experimental conditions, and the toxic nature of effluents offsets its application. In this context, COD comes into existence where organic matter in the effluent was oxidised by a strong oxidising agent at elevated temperature under acidic environment. This test requires approximately 3 hours for analysis and is not dependant on biological environment. However, this method has its own limitations, such as undependable accuracy, input of chemicals and energy and production of secondary effluent disposing problems, etc. This process of BOD/COD characterisation of an effluent is time consuming, a laboratory installation with special instrumentation to maintain the required temperature constantly, input of chemicals and energy and can not be generally utilised in the field conditions.

The other wastewater characterisation techniques for biodegradability are measurement of its inorganic nitrogen compound uptake rates. However, these methods will be applicable only for certain types of wastes. Moreover, they require special instrumentation to measure the respective inorganic compounds in the effluents. Recently, efforts are being made to combine an already advanced respirometric technique, the hybrid respirometer with titrimetric technique with limited success [Vanrolleghem, P. A. and Spanjers, H. (1998) Wat. Sci. Technol., 37; 237-246]. Several other researchers have also attempted to develop micro-organism based biosensors, which involve determination of microbial activity either by spectrophotometrically or electrochemically [Bains, W. (1994) Biosensors Bioelectronics., 9; 111-117; Corbisier, P., Thiry, E., and Diels, L. (1996) Environ. Toxicol. Water Qual., 11; 171-177; Silva, M. J., and Wong, J. L. (1995) Bioelectroch m. Bioener., 37; 141-148]. The drawbacks with all these techniques are long incubation periods and low initial response, etc. [Rogers, K. R. and Koglin, E. N. (1997) in Biosensors for Direct Monitoring of Environmental Pollution in Field, (ed. D. P. Nikolelis, U. J. Krull, J. Wang, and M. Mascini) Kluwer Publishers, Boston, 335-349]. Moreover, implementation of these technologies for on-site effluent characterisation is not possible [Koglin, E. N. and Williams, L. R. (1994) Trends. Anal. Chem. 13; 294-299]. Hence the development of a reliable methodology to rapidly estimate the oxygen required for biodegradation considerably promises advancement in environmental monitoring.

OBJECTS OF THE INVENTION

The main object of the invention is to provide a process for the preparation of stable and reusable biosensing granules useful in measuring the biotreatability of effluents.

Another object of the invention is to provide a cost-effective process for the evaluation of the biotreatability of effluents.

It is a further object of the invention to provide a tool kit for the effective characterisation of the biotreatability of effluent under field conditions.

It is another object of the invention to provide a stable and reusable biosensing granules for determination of the biodegradable nature of an effluent.

It is a further object of the invention to provide information regarding discharge characters on site.

Yet another object of the invention is to provide a eco-friendly technique that does not require chemicals for waste characterization for biological treatment.

Another object of the invention is to provide a fast method to determine the biotreatability of an effluent.

SUMMARY OF THE INVENTION

Accordingly, the present invention provides a process for the prevention of stable and reusable biosensing granules useful in the assessment of biodegradability of effluents, said process comprising developing active aerobic microbial consortia in synthetic medium, separating the active aerobic microbial consortia, immobilising the said microbial consortia using natural polymer to form biosensing granules, dehydrating the immobilised biosensing granules at 24-32° C. for a period of 4-12 hours, to obtain stable biosensing granules having a moisture content of 5-30%.

The present invention also relates to a method for the preparation of stable and reusable biosensing granules useful for assessing the biotreatability of effluent which comprises:
  i. selecting a seed culture from raw sewage, wastewater treatment plants or activated sludge units;
  ii. preparing a synthetic growth media;
  iii. inoculating a microbial consortia in the said media;
  iv. incubating the microbial consortia under aerobic condition having an air flow of about 5 ml/minute, at about 28° C. for a period of 12-24 hours or till the level of mixed liquor suspended solids (MLSS) reaches 14500-15500 mg/liter on a dry weight basis;
  v. separating the active aerobic microbial consortia by centrifugation at the appropriate rpm for 10-15 minutes and at a temperature of about 28° C.;
  vi. immobilizing the said microbial consortia using aqueous natural polymer solution by any known methods to obtain immobilized biosensing beads;
  vii. separating the said biosensing beads by decanting the said solution;
  viii. washing the beads with water thoroughly several times;
  ix. dehydrating the beads at a temperature in the range of 24-36° C. for a period of 2-20 hours to obtain stable biosensing granules having a moisture content of 5-30%;
  x. activating the stable biosensing granules by incubation in 2-5% (w/v) aqueous solution at 28° C. for 2-10 hours to get active stable biosensing granules;
  xi. separating the active granules from the activation solution by conventional methods.

In one embodiment of the invention, the aerobic microbial consortia is collected from raw sewage, wastewater treatment plants or from activated aerated sludge units.

In another embodiment of the invention, the synthetic growth media used consists of (in grams/liter): glucose—29-31; ammonium chloride—5.5-7.5; potassium dihydrogen orthophosphate—1.5-3.5; dipotassium hydrogen orthophosphate—0.5-1.5; sodium bicarbonate—4.5-5.5; yeast extract—0.5-1.5; urea—0.3-0.7; and tryptone—0.5-1.5.

In another embodiment of the invention, the pH of the prepared synthetic growth media is adjusted to about 7.0 using 0.1 N hydrochloric acid or 0.1 N sodium hydroxide.

In another embodiment of the invention, about 10% (w/v) of the collected microbial consortia is inoculated in the synthetic growth medium.

In a further embodiment of the invention, the inoculated synthetic growth medium is aerated by passing air at the rate of about 5 ml/minute.

In yet another embodiment of the invention, the growth media is incubated at a temperature of 24-32° C.

In another embodiment of the invention, the growth of the active aerobic microbial consortia is terminated after the mixed liquor suspended solids (MLSS) reaches 14500-15500 mg/liter.

In another embodiment of the invention, the active aerobic microbial consortia is separated from the broth using conventional methods selected from centrifugation, settling, decanting the supernatant.

In a further embodiment of the invention, the separated active aerobic microbial consortia is immobilized using 1-3% (w/v) sodium alginate and 0.2M calcium chloride solution.

In yet another embodiment of the invention, the active aerobic microbial consortia is used for immobilisation in the range of 3-5% (w/v) to obtain immobilized biosensing granules.

In another embodiment of the invention, the prepared immobilised biosensing granules are incubated for 12-24 hours at 4° C. in 0.2 M calcium chloride solution.

In another embodiment of the invention, the prepared immobilised biosensing granules are separated from the calcium chloride solution by decanting the aqueous liquid.

In another embodiment of the invention, the immobilised biosensing granules are dehydrated at 24-32° C. for a period of 2-20 hours to obtain stable biosensing granules with 5-30% moisture content.

In a further embodiment of the invention, the stable biosensing granules are incubated for 2-10 hours in 2-5% (w/v) glucose solution, at 24-32° C. to obtain active stable biosensing granules.

In yet another embodiment of the invention, the stable biosensing granules are separated from the activation media by draining out the solution.

In a further embodiment of the invention, the residual dissolved oxygen content of the effluent is measured using oxygen probe before and 2-6 hours of addition of activation stable biosensing granules in the range of from 2-5% (w/v).

The present invention also relates to a method for the estimation of the biotreatability of an effluent using the biosensing granules of claim 1 wherein the effluent is characterized as highly biotreatable if the dissolved oxygen consumption rate by the activated biosensing granules is more than 2 mg/l, medium when the siad oxygen consumption rate is between 1.0 to 2.0 mg/l, and low when the oxygen consumption rate is less than 1.0 mg/l.

DETAILED DESCRIPTION OF THE INVENTION

The biosensing granules of the invention are mechanically strong and biologically active and can be employed in assessing the biodegradability of the effluent within 2-4 hours at a temperature in the range of from 24-32° C. without involving BOD instrumentation or COD analysis.

The process of the present invention involves the preparation of a stable and reusable biosensing granule and its use for assessing the biotreatability of effluents. The seed culture is selected from raw sewage, wastewater treatment plant or from activated sludge unit. A synthetic growth media consisting of (in grams/liter): glucose—30.0; ammonium chloride—6.5; potassium dihydrogen orthophosphate—2.5; dipotassium hydrogen orthophosphate—1.0; sodium bicarbonate—5.5; yeast extract—1.0; urea—0.5; and tryptone—1.0 at pH 7.0 is prepared, under aerated condition having air flow of 5 ml/minute, at 28° C. for a period of 12-24 hours or till the mixed liquor suspended solids (MLSS) reaches 14500-15500 mg/liter on a dry weight basis. The resultant active aerobic microbial consortia was separated by centrifugation at an appropriate rpm, preferably 10000 rpm for 10-15 minutes at 28° C. The said microbial consortia is immobilised using aqueous natural polymer solution by known methods to obtain immobilised microbial biosensing beads. These beads are separated by decanting the solution and washed thoroughly with water several times and dehydrated at a temperature in the range of from 24-36° C. for a period of 2-20 hours to obtain stable biosensing granules having moisture in the range of from 5-30%.

The stable and reusable biosensing granules of the invention are granular spherical particles having a diameter of 0.3-1.0 mm, blackish in colour, hard, robust particles which are insoluble in aqueous or organic medium. These granules have intrinsic capacity to absorb or desorb water molecules. These stable granules are activated by incubating them in 2-5% (w/v) aqueous solution at 28° C. for 2-10 hours to get active stable biosensing granules. These active granules are separated from the activation solution by conventional methods. Various types of industrial effluents are collected from industrial sites and incubated at about 1-5% (w/v) to obtain active stable biosensing granules. The desolved oxygen in the effluent is measured before the addition of the activated biosensing granules and again after two hours of granule addition.

The source for the active aerobic microbial consortia is raw sewage, or wastewater treatment plant or aerated sludge treatment unit.

The synthetic media used for growing the collected active aerobic microbial consortia consists of (in grams/liter): glucose—30.0; ammonium chloride—6.5; potassium dihydrogen orthophosphate—2.5; dipotassium hydrogen orthophosphate—1.0; sodium bicarbonate—5.5; yeast extract—1.0; urea—0.5; and tryptone—1.0 at pH 7.0± is prepared, under aerated condition having air flow of 5 ml/minute, at 28° C. for a period of 12-24 hours or till the mixed liquor suspended solids (MLSS) reaches 14500-15500 mg/liter on a dry weight basis.

Preferably, the biosensing granules are prepared by mixing microbial consortia of mixed liquor suspended solids (MLSS) 600-8500 mg/liter in 2% (w/v) natural or synthetic polymer solution till it became a uniform mixture. This slurry is dropped into a 0.2 M curing solution in the form of droplets using a peristaltic pump to make uniform size granules of 1.0 to 1.5 mm diameter. These granules are cured at 4° C. in 0.2M curing solution overnight and washed twice with water and then dried at room temperature.

Different industrial effluents from common effluent treatment plant mainly consisting of chemical industrial waste waters, textile industry effluents mainly consisting of H-acid and effluent from industries involved in extraction of natural products of plants are collected in bottles for the purpose of this invention. The collected effluents are characterised for their chemical oxygen demand and biological oxygen demand using classical methodologies.

EXAMPLE 1

Stable Biosensing Granule Preparation

The active aerobic microbial consortia was collected from wastewater treatment plant. The synthetic growth medium consisting of the following ingredients (in grams/liter): glucose—30.0; ammonium chloride—6.5; potassium dihydrogen orthophosphate—2.5; dipotassium hydrogen orthophosphate—1.0; sodium bicarbonate—5.5; yeast extract—1.0; urea—0.5; and tryptone—1.0 was prepared. The pH of the synthetic medium was adjusted to 7.0 using 0.1N hydrochloric acid or 0.1N sodium hydroxide solution. The collected microbial consortia was inoculated in the synthetic growth media and incubated under aerobic conditions with an air flow of 5 ml/minute, till the MLSS reached 15500 mg/l on dry weight basis at 28° C. The active microbial consortia was separated by centrifugation at 10000 rpm for 10 minutes at 28° C. and the active microbial consortia slurry was prepared using 4% (w/v) active microbial consortia and 2% (w/v) sodium alginate solution in water. This slurry was then dropped in the form of droplets in 0.2M calcium chloride solution and the immobilised biosensing beads were further incubated in the same solution for a period of 18 hours at 4° C. The beads were then separated by draining the calcium chloride solution and washed repeatedly several times with water. The immobilising biosensing beads were then dehydrated at 28° C. for 12 hours to obtain stable biosensing granules.

EXAMPLE 2

The active aerobic microbial consortia was collected from sewage treatment plant. The synthetic growth medium consisting of the following ingredients (in grams/liter): glucose—30.0; ammonium chloride—6.5; potassium dihydrogen orthophosphate—2.5; dipotassium hydrogen orthophosphate—1.0; sodium bicarbonate—5.5; yeast extract—1.0; urea—0.5; and tryptone—1.0 was prepared. The pH of the synthetic medium was adjusted to 7.0 using 0.1N hydrochloric acid or 0.1N sodium hydroxide solution. The collected microbial consortia was inoculated in the synthetic growth media and incubated under aerobic conditions with an air flow of 5 ml/minute, till the MLSS reached 14500 mg/l on dry weight basis at 30° C. The active microbial consortia was separated by centrifugation. The active microbial consortia slurry was prepared using 5% (w/v) active microbial consortia and 4% (w/v) sodium alginate solution in water. This slurry was then dropped in the form of droplets in 0.2M calcium chloride solution and the immobilised biosensing beads were further incubated in the same solution for a period of 12 hours at 4° C. The beads were then separated by draining the calcium chloride solution and washed repeatedly several times with water. The immobilised biosensing beads were then dehydrated at 24° C. for 18 hours to obtain stable biosensing granules.

EXAMPLE 3

Active microbial consortia was collected from raw sewage. The synthetic growth medium consisting of following ingredients (in grams/liter): glucose—30.0; ammonium chloride—6.5; potassium dihydrogen orthophosphate—2.5; dipotassium hydrogen orthophosphate—1.0; sodium bicarbonate—5.5; yeast extract—1.0; urea—0.5; and tryptone—1.0 was prepared. The pH of the synthetic medium was adjusted to 7.0 using 0.1N hydrochloric acid or 0.1N sodium hydroxide solution. The collected microbial consortia was inoculated in the synthetic growth media and incubated under aerobic conditions with an air flow of 5 ml/minute, till the MLSS reached 15000 mg/l on dry weight basis at 28° C. The active microbial consortia was separated by centrifugation at 5000 rpm for 15 minutes at 28° C. and the active microbial consortia slurry was prepared using 5% (w/v)

active microbial consortia and 1% (w/v) sodium alginate solution in water. This slurry was then dropped in the form of droplets in 0.2M calcium chloride solution and the immobilised biosensing beads were further incubated in the same solution for a period of 24 hours at 4° C. The beads were then separated by draining the calcium chloride solution and washed repeatedly several times with water. The immobilising biosensing beads were then dehydrated at 30° C. for 18 hours to obtain stable biosensing granules.

EXAMPLE 4

Characterisati n f bi Sensing Granules Using Synthetic Medium

The BOD and COD of the synthetic media were determined using standard methods prescribed by the American Public Health Association (APHA) (1967) Standard Methods for Examination of Water and Wastewater, Washington, D.C. 300 ml of this synthetic media was taken in a standard BOD bottle and to this 0.2 grams of activated biosensing granules (BSG) were added. The dissolved oxygen concentration in the solution was measured at room temperature using dissolved oxygen probe.

| S. No. | $BOD_5$ (mg/l) | COD (mg/l) | $BOD_5$/COD | Dissolved oxygen consumed/2 hours by BSG (mg/l) |
|---|---|---|---|---|
| 1 | 7410 | 9500 | 0.780 | 2.94 |
| 2 | 7450 | 9550 | 0.780 | 2.95 |
| 3 | 7350 | 9450 | 0.777 | 3.93 |

EXAMPLE 5

Characterisation of Industrial Common Effluent Using Biosensing Granules

An effluent was collected from common effluent treatment plant, which consists of discharges from various industries. The effluent was characterised for COD and $BOD_5$ according to the procedure described by American Public Health Association (AHPA) (1967) Standard Methods for Examination of Water and Wastewater, Washington, D.C.

In a BOD bottle, 300 ml of the above effluent was taken and to this 0.2 grams of activated biosensing granules were added. The dissolved oxygen in the bottle was determined, at room temperature, initially and after two hours using dissolved oxygen probe.

| S. No. | $BOD_5$ (mg/l) | COD (mg/l) | $BOD_5$/COD | Dissolved oxygen consumed/2 hours by BSG (mg/l) |
|---|---|---|---|---|
| 1 | 6440 | 10625 | 0.606 | 1.47 |
| 2 | 6340 | 10400 | 0.609 | 1.46 |
| 3 | 6540 | 10760 | 0.607 | 1.48 |

EXAMPLE 6

Characterisation of Textile Industry Effluent Using Biosensing Granules

A textile industry effluent mainly consisting of H-acid was collected and characterised for COD and $BOD_5$ based on the procedure described by AHPA (1967) Standard Methods for Examination of Water and Wastewater, Washington, D.C. methods. In a BOD bottle, 300 ml of H-acid effluent was taken and to this 0.2 grams of activated biosensing granules were added. The dissolved oxygen in the bottle was measured initially and after two hours, at room temperature, using dissolved oxygen probe.

| S. No. | $BOD_5$ (mg/l) | COD (mg/l) | $BOD_5$/COD | Dissolved oxygen consumed/2 hours by BSG (mg/l) |
|---|---|---|---|---|
| 1 | 215 | 766 | 0.280 | 0.60 |
| 2 | 210 | 764 | 0.274 | 0.59 |
| 3 | 220 | 769 | 0.286 | 0.61 |

EXAMPLE 7

Characterisation of Industrial Effluent Using Biosensing Granules

The effluent of an industry involved in extraction of natural products of plants was collected and analysed for various parameters like COD and $BOD_5$ using AHPA (1967) Standard Methods for Examination of Water and Wastewater, Washington, D.C. procedures. In a BOD bottle, 300 ml of the above effluent was taken and to this 0.2 grams of activated biosensing granules were added. The dissolved oxygen in the bottle was measured initially and after two hours using dissolved oxygen probe at room temperature.

| S. No. | $BOD_5$ (mg/l) | COD (mg/l) | $BOD_5$/COD | Dissolved oxygen consumed/2 hours by BSG (mg/l) |
|---|---|---|---|---|
| 1 | 7260 | 16200 | 0.448 | 0.84 |
| 2 | 7210 | 16250 | 0.447 | 0.82 |
| 3 | 7310 | 16340 | 0.447 | 0.86 |

Advantages of the Invention:

The main advantages of this invention are:

1. The present invention provides a rapid methodology for characterisation of an effluent for its biotreatability.
2. The prepared stable biosensing granules can be stored at room temperature for a prolonged period without loss of activity.
3. The prepared stable biosensing granules can be reused several times for detection of biotreatability of an effluent.
4. The prepared biosensing granules are capable of being used in situ.
5. The prepared biosensing granules are easy to use and do not require specialised and/or skilled labour for use thereof.
6. The prepared biosensing granules of the invention render the detection of biotreatability of effluents cost effective.
7. The present invention for the detection of biotreatability of effluents by stable biosensing granules provides an easy and simple technique for effluent characterisation for their biotreatability.
8. The present invention for the detection of biotreatability of effluents by stable biosensing granules requires minimum precaution.
9. The present invention for the detection of biotreatability of effluents by stable biosensing granules can be used for the rapid evolution of biological degradable organic content in the effluent.

10. The present invention for the detection of biotreatability of effluents by stable biosensing granules does not require any additional inputs of chemicals for the characterisation of the effluent.

11. The invention is useful for the evaluation of large samples in a short time.

12. Any effluent can be characterised using the stable biosensing granules of the invention.

We claim:

1. A process for preparing stable and reusable biosensing granules useful in assessing biodegradability of an effluent, said process comprises the steps of:
   i. culturing active aerobic microbial consortia in a synthetic growth media, wherein the aerobic microbial consortia is collected from raw sewage, wastewater treatment plants or from activated aerated sludge units,
   ii. separating the active aerobic microbial consortia from the synthetic media,
   iii. immobilizing the active microbial consortia using a natural polymer to form immobilized biosensing granules, and
   iv. dehydrating the immobilized biosensing granules at 24-36° C. for a period of 2 to 20 hours, to obtain stable biosensing granules having a moisture content of 5-30%.

2. The process as claimed in claim 1, wherein the culturing of the active aerobic microbial consortia comprises the steps of:
   i. inoculating a synthetic growth media with a microbial consortia collected from the group consisting of raw sewage, wastewater treatment plants and from activated aerated sludge units;
   ii. incubating the inoculated microbial consortia under aerobic conditions at an air flow rate of about 5 ml/minute, at 24° C. to 32° C. for a period of 12-24 hours or until the level of mixed liquor suspended solids (MLSS) reaches 14500-15500 mg/liter on a dry weight basis; and
   iii. separating the active aerobic microbial consortia by centrifugation for 10-15 minutes and at a temperature of 28° C.

3. The process as claimed in claim 1, wherein the active aerobic microbial consortia is immobilized using an aqueous natural polymer solution to obtain immobilized biosensing beads, separating the biosensing beads, washing the beads with water, dehydrating the beads at a temperature in the range of 24° C.-32° C. for a period of 4-12 hours to obtain stable biosensing granules having a moisture content of 5-30%; incubating the stable biosensing granules in 2-5% (w/v) aqueous activation solution at 28° C. for 2-10 hours to obtain active stable biosensing granules; and separating the active stable biosensing granules from the activation solution.

4. The process as claimed in claim 1, wherein the synthetic growth media consists of, in grams/liter: glucose—30.0; ammonium chloride—6.5; potassium dihydrogen orthophosphate—2.5; dipotassium hydrogen orthophosphate—1.0; sodium bicarbonate—5.5; yeast extract—1.0; urea—0.5; and tryptone—1.0.

5. The process as claimed in claim 1, wherein the pH of the synthetic growth media is adjusted to about 7.0 using 0.1 N hydrochloric acid or 0.1 N sodium hydroxide.

6. The process as claimed in claim 2, wherein about 10% (w/v) of the microbial consortia is inoculated in the synthetic growth media.

7. The process as claimed in claim 2, wherein the inoculated microbial consortia is aerated by passing air at a rate of about 5 ml/minute.

8. The process as claimed in claim 2, wherein the growth media is incubated at a temperature of about 28° C.

9. The process as claimed in claim 2 wherein the growth of the active aerobic microbial consortia is terminated after MLSS reaches 14500-15500 mg/liter.

10. The process as claimed in claim 1, wherein the active aerobic microbial consortia is separated from the synthetic growth by a method selected from the group consisting of centrifugation, settling and decanting of obtained supernatant.

11. The process as claimed in claim 3, wherein the separated active aerobic microbial consortia is immobilized on a natural polymer using 1-3% (w/v) sodium alginate and 0.2M calcium chloride solution.

12. The process as claimed in claim 1, wherein the active aerobic microbial consortia to obtain immobilized biosensing granules is in a range of 3-5% (w/v).

13. The process as claimed in claim 1, further comprising incubating the immobilized biosensing granules for 12-24 hours at 4° C. in 0.2M calcium chloride aqueous solution.

14. The process as claimed in claim 13, wherein the immobilized biosensing granules are separated from the calcium chloride solution by decanting aqueous liquid.

15. The process as claimed in claim 1, further comprising incubating the stable biosensing granules for 2-10 hours in an activation solution comprising 2-5% (w/v) glucose solution, at 24-32° C. to obtain active stable biosensing granules.

16. The process as claimed in claim 15, wherein the stable biosensing granules are separated from the activation solution by draining.

* * * * *